United States Patent [19]

Niemi

[11] 4,068,669
[45] Jan. 17, 1978

[54] STIMULATOR FAULT PROTECTION CIRCUIT

[75] Inventor: Bill Howard Niemi, Brooklyn Park, Minn.

[73] Assignee: Stimulation Technology, Inc., Minneapolis, Minn.

[21] Appl. No.: 634,577

[22] Filed: Nov. 24, 1975

[51] Int. Cl.² .............................................. A61N 1/36
[52] U.S. Cl. .............................. 128/419 R; 128/2.1 P
[58] Field of Search .................. 128/303.17, 421, 422, 128/419 R, 2.1 P, 423; 317/9 A, 18 R, 30, 50; 331/62

[56] References Cited

U.S. PATENT DOCUMENTS

| | | | |
|---|---|---|---|
| 3,817,254 | 6/1974 | Maurer | 128/421 |
| 3,885,569 | 9/1975 | Judson | 128/303.14 |
| 3,886,932 | 6/1975 | Suessmilch | 128/2.1 P |
| 3,889,184 | 6/1975 | Bass | 128/2.1 P |

Primary Examiner—William E. Kamm

[57] ABSTRACT

A current monitoring and control circuit for use with a medical stimulation device for monitoring the exciting current to stimulation electrodes connected to the device is provided having a disabling component to inactivate a signal generating circuit resident within the stimulator. Operation of this disabling component may be controlled by the functioning of sampling and detection components preferably connected to the output of the signal generator and triggered by an undesirable output signal surge. Included may be visual signaling and metering functions.

15 Claims, 4 Drawing Figures

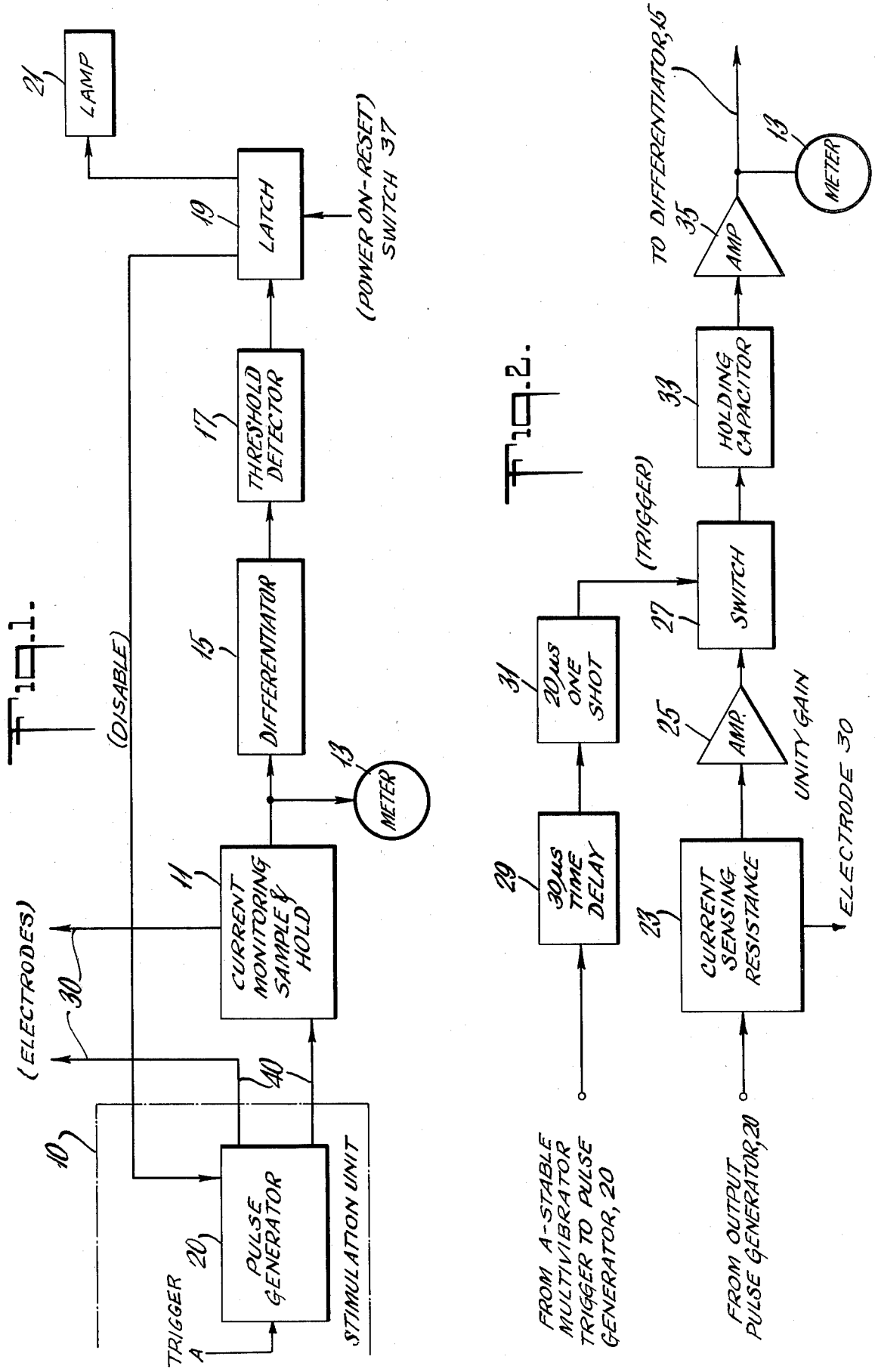

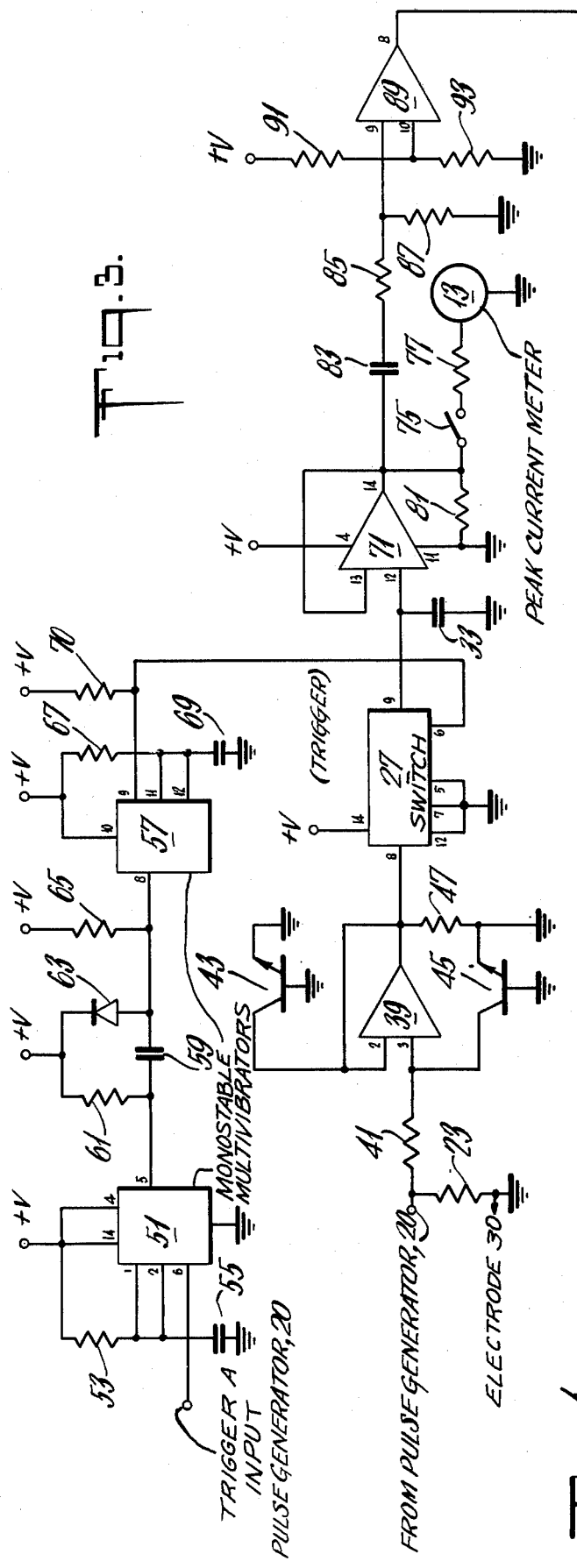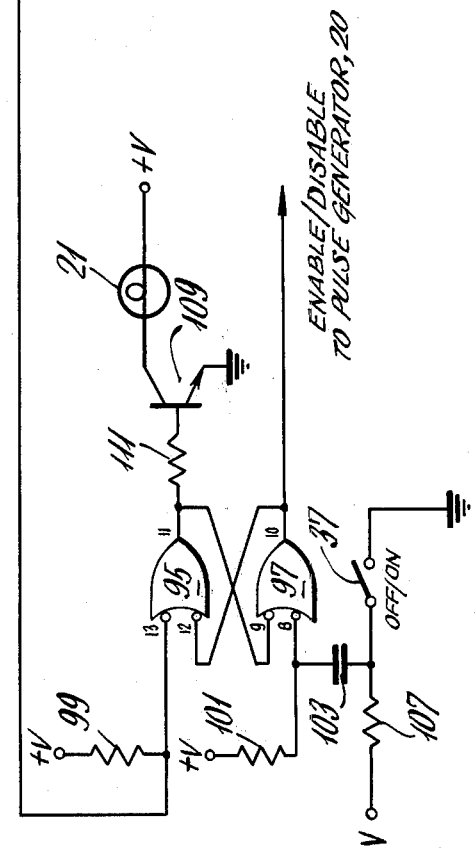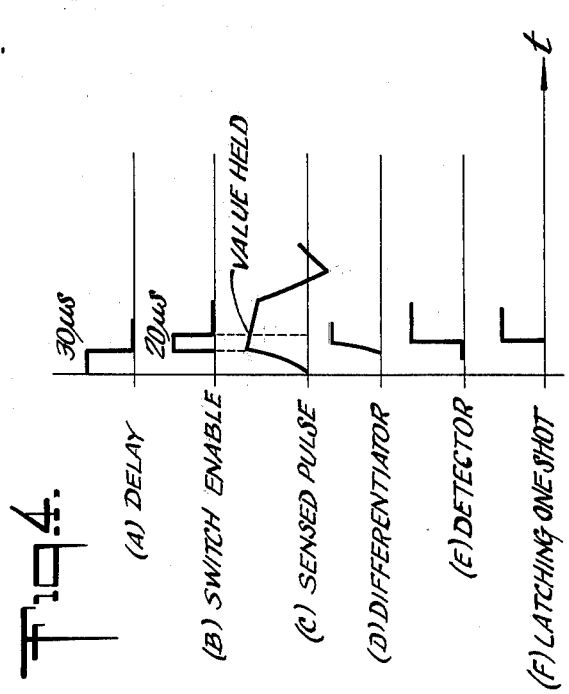

STIMULATOR FAULT PROTECTION CIRCUIT

BACKGROUND OF THE INVENTION

In the use of medical stimulators for pain control and body function stimulation, sudden increases in output current to the patient, via the electrodes used with these stimulators, have been known to occur. These surges in output current can result in discomfort, skin burns, muscle spasms, and pain and fright to a patient. With weak or sensitive patients or with patients with cardiac conditions these results can be dangerous or even disastrous.

Most often these sudden increases in output current are the result of intermittent electrode connections, improper unit operation or surges within the unit due to circuitry failures. These types of surge generating conditions, especially where the stimulator units are operated by the patients themselves, can never be completely controlled or eliminated.

An objective of this invention, therefore, is to provide a circuit connected to existing stimulator circuitry for detecting current output surges to electrodes connected thereto.

Another objective of this invention is to provide a circuit for disabling the output pulse generator within the stimulator unit when an output surge is detected.

A further objective of the invention is to provide detection and control circuitry which will tolerate output current ramps normally present during stimulator unit adjustment while discriminating against excessively sharp ramps or surges.

SUMMARY OF THE INVENTION

The objectives of this invention are achieved by a detection and control circuit connected into the output of a medical stimulation unit, such as an electronic pain control device, to monitor the output current transmitted to stimulation electrodes connected thereto. Output current may be sampled as it is conducted to the electrodes from an output pulse generator resident within the stimulation unit. Preferably, detection of output signal surges initiates interruption of the operation of the pulse generator.

A current monitoring sample and hold component may monitor the output signals produced by the pulse generator. The peak values of these signals may be passed onto a differentiator and a threshold detector which preferably discriminate between normal signal levels and surges in output signals.

A latching component whose operation may be activated by the output of the discriminator may disable the operation of the stimulation unit's pulse generator when an output signal surge is detected. This latching component is preferably locked once activated, but may be manually reset.

Signal values resident in the sample and hold component may be metered. A visual display of the state of the latching component and, therefore, of the operation of the stimulation unit's output pulse generator may also be provided.

DESCRIPTION OF THE INVENTION

The novel features of this invention as well as the invention itself, both as to its organization and method of operation, will best be understood from the following description taken in connection with the accompanying drawings in which like characters refer to like parts, and in which:

FIG. 1 is a block diagram of the entire monitoring and control circuit;

FIG. 2 is a block diagram of the sample and hold component of the circuit;

FIG. 3 is a detailed schematic of the entire circuit;

FIG. 4 is a timing diagram for the operation of the circuit.

The monitoring and control circuit comprising this invention is connected into the output of a stimulation unit 10, FIG. 1, of standard configuration, being adjustable as to pulse amplitude and frequency, and having a pulse generator 20 as its output stage. This pulse generator 20 can have an astable multivibrator driving a monostable multivibrator output, trigger A.

The circuit of the invention monitors the signals emanating from the stimulator pulse generator 20; i.e., its monostable multivibrator output, and transmitted to patient electrodes 30 via transmission cables 40. Current pulses sent to the electrodes 30 are monitored for excessive signal strengths or surges. This function may be accomplished by inserting a current monitoring, sample and hold component 11 into a primary signal electrode transmission cable 40.

The sample and hold component 11 reads each signal pulse sent to the electrodes 30 and holds the peak current value of that pulse in order that the remainder of the circuitry can operate upon it. Frequency independent operation is, therefore, provided by this component 11, isolating the rest of the circuit from such error producing conditions as the presence of ripple on signal pulses at low repetition rates.

A peak current meter 13 is connected to the output of the sample and hold component 11 to provide a visual display of the signal output of the stimulator 10 and a real time indication of any malfunction.

Connected to the sample and hold circuit 11 is differentiator 15. The differentiator 15 has its ramp function set at an empirically determined value. Too shallow a ramp function will produce an impulse spike during normal adjustment of the pulse generator 20 by a doctor or a patient. Too sharp of a ramp function will reduce sensitivity and weaken the protection the circuit provides. Values for the differentiator 15 will be given below.

Threshold detector 17 is connected to the output of the differentiator 15. This detector 17 is set to recognize undesirably large signals to control the operation of a latching flip-flop 19 which is connected to it.

The triggering of the latching flip-flop 19 disables the operation of the pulse generator 20 by disabling its output monostable multivibrator and, consequently, cuts off signals to the electrodes 30. Triggering of latching flip-flop 19 also supplies power to a lamp 21 which acts as the visual indicator of the condition of the latch 19.

The sample and hold component 11 is constructed as shown by FIG. 2. Output pulses from the stimulator's pulse generator 20 are sensed across a resistance 23. The voltage derived, drives a unity gain amplifier 25. The output from this amplifier 25 in turn connected to a selectively controllable bilateral switch 27. This switch 27 is triggered at a specific time and for a predetermined period to pass only the signal value representative of the peak signal current value, i.e., a peak voltage value as function of current, produced by the amplifier 25.

The trigger pulse to the bilateral switch 27 is produced as a function of a pulse from an astable multivibrator (trigger A) resident within the stimulator 20 to drive the output pulse generator 20. This astable multivibrator pulse triggers the output pulse generator 20 and is also connected to the input of a 30-microsecond time delay 29 which in turn is connected to trigger a 20-microsecond pulse duration "one-shot" monostable multivibrator 31. The output of the one-shot 31 is connected to trigger the bilateral switch 27.

This bilateral switch 27 is connected to a holding capacitor 33 which charges up to the peak voltage, representative of the peak current value, produced by the amplifier 25 and passed through the switch 27.

The time delay of 30-microseconds was set into the delay component 29 to allow for the rise time of each pulse generated by the pulse generator 20. Therefore, it is the peak value of each pulse which is selected to charge the capacitor 33. For stimulation pulses having faster or slower rise times, shorter or longer time delays can be introduced to permit the proper triggering of the switch 27 to pass the peak value of each pulse. The 20-microsecond pulse duration produced by the one-shot 31 is sufficient time for the switch 27 to be enabled and the capacitor 33 to be charged.

A unity gain amplifier 35 is connected to this holding capacitor 33 to isolate it from the peak current meter 13 and to provide a driver for the meter 13 and the differentiator 15.

The trigger pulse to the bilateral switch 27 was chosen to be produced as a function of the astable multivibrator trigger pulse to the pulse generator 20 in order that this triggering pulse would not be disabled when the output pulse generator 20 was disabled. With this circuit arrangement, after the pulse generator 20 is disabled, the switch 27 will continue to be triggered and, thusly, drain any charge build up on the holding capacitor 33 due to biasing on the driver amplifier 35. Therefore, erroneous meter 13 readings due to capacitor 33 charge build up are avoided.

The protection circuitry of this invention can be reset by resetting the latching flip-flop 19. This resetting of the latch 19 is accomplished by an impulse from the poweron, i.e., on/off switch 37 which controls the power to the entire stimulation unit. This impulse is conducted to the latching flip-flop 19 via the connection of its reset terminal to the power-on switch 37 of the unit.

Circuit components incorporated into a principal embodiment are shown in FIG. 3. Signals from the pulse generator 20 output are sensed across a 39.2 ohm resistor 23 by a common mode operational amplifier 39, of the National Semiconductor LM 324N type, having a 100 kilo ohm input resistor 41. The input terminals of this amplifier 39 are limited by common base connected 2N2222A transistors 43, 45, each being connected via the emitter-collector terminals to ground.

The output of the amplifier 39 is sensed across a 470 ohm resistor 47 by an RCA type CD4016AE cos/mos bilateral switch 27. This switch 27 is enabled to pass a signal when a voltage pulse is present on its trigger terminal.

As stated above the trigger pulses (trigger A) to the pulse generator 20 are processed to trigger the switch 27. These pulses (trigger A) are connected to a 30 microsecond time delay 51, which can be created with a Signetics monostable multivibrator NE556 type "one-shot". This one-shot 51 acts as a thirty microsecond time delay because the falling edge of the output pulse of this one-shot 51 is used to trigger the next component, and also, this one-shot 51 has a 30 microsecond pulse width by virtue of the 33 kilo ohm resistor 53 and the 0.001 microfarad capacitor 55 connected to it.

The output of the one-shot 51 is coupled to an identical monostable multivibrator (one-shot) 57 via a 0.001 microfarad capacitor 59. A 22 kilo ohm resistor 61 connected from the supply voltage to the output of the first one-shot 51 as well as a diode 63 and a 47 kilo ohm resistor connected in parallel between the supply voltage and the input to the second one-shot 57 complete the coupling connection.

The second one-shot 57 has a 20 microsecond pulse width by virtue of the 15 kilo ohm resistor 67 and the 0.001 microfarad capacitor 69 connected thereto. The pulses generated by this second one-shot 57 are connected to trigger the bilateral switch 27. The trigger terminal of this bilateral switch is biased by a 6.8 kilo ohm resistor 70 connected to the supply voltage.

A unity gain operational amplifier 71, identical to the amplifier 39 is connected to the output of the switch 27. Connected to the input of this second amplifier 71 is a 0.1 microfarad capacitor 33 to ground which acts to hold the voltage passed through the switch 27.

Connected to the output of this second amplifier 71 through a manually operated switch 75 and a 44.2 kilo ohm resistor 77 is a peak current meter 13. The output of this second amplifier is also biased through a 10 kilo ohm resistor 81 to ground.

A high pass filter, which operates as the differentiator 15, comprises a 0.1 microfarad capacitor 83 and a 100 kilo ohm resistor 85 in series and a 100 kilo ohm resistor 87 to ground, is connected to the output of the amplifier 71.

A differentially connected operational amplifier 89 of a type identical to amplifiers 39 and 71 has a signal input tied to the junction of the two 100 kilo ohm resistors 85, 87. The reference input of this amplifier 89 is connected to two resistors forming a voltage divider wherein a 100 kilo ohm resistor 91 connected to the supply voltage and a 3.9 kilo ohm resistor 93 connected to ground. An output appears from this amplifier 89 when the reference input voltage is exceeded by the signal input voltage.

The output of the amplifier 89 is tied to a latching flip-flop 19 formed by two nand gates 95, 97, of the RCA cos/mos, CD4011AE type, interconnected in a standard manner and each being biased with 100 kilo ohm resistor 99, 101, respectively, from the supply voltage. An input of complementary nand gate 97 is capacitor coupled via a .1 microfarad capacitor 103 to the power on/off switch 37 of stimulator unit. To assure a stable voltage level the latching flip-flop side of the power switch 37 is biased to a supply voltage through a 10 kilo ohm resistor 107. The output of the complementary nand gate 97 is connected to disable the output pulse generator 20.

The output of the principal nand gate 95 is connected to a buffer driver transistor 109 of the type 2N2222A, which is connected in common emitter configuration to control the flow of current through a signal lamp 21. The transistor 109 has a 22 kilo ohm resistor 111 in its base connection.

The sequence of signals passing through the circuit of FIG. 3 can be understood from the timing diagram shown in FIG. 4. Line A of this diagram shows the time delay created by the first one-shot 51. Line B shows the bilateral switch 27 enable pulse created by the second one-shot 57. Line C is the pulse generator 20 output pulse received by the first amplifier 39 and passed onto the bilateral switch 27. Line D shows what the pulse received by the bilateral switch 27 looks like as it is passed by the holding capacitor 33 and through the second amplifier 71 circuit to be received by the differentiator 15. An excessive signal surge is detected line E to trigger the latching flip-flop 19, line F.

It is intended that all matter contained in the above description or shown in the accompanying drawings shall be interpreted as illustrative and not in the limiting sense. Equivalent substitutions producing different embodiments of this invention could be made without departing from the scope thereof.

What is claimed is:

1. A fault protection circuit for a medical unit having triggered output signal generator circuitry therein to provide a series of output signals, comprising:
   means for monitoring said output signals from said medical unit output signal generator, said monitoring means being connected to said output signal generator;
   means associated with said monitoring means for differentiating between successive signal values of said output signals monitored for detecting when said successive signal value differentials exceed a threshold; and
   means connected to said differentiating and detecting means for affecting the operation of said medical unit signal generator upon the detection of said threshold being exceeded.

2. The circuit of claim 1 wherein said monitoring means includes means for sampling each output signal from said medical unit output signal generator, said sampling means being connected thereto; and means for holding the peak signal value of each said signal sampled, said holding means being connected to said sampling means; and wherein said medical unit signal generator operation affecting means includes means connected to said differentiating and detecting means for disabling said medical unit signal generator.

3. The circuit of claim 2 wherein said sampling means includes means for sensing each output signal emanating from said medical unit output signal generator;
   and wherein said peak signal value holding means includes means connected to said sensing means for passing only the peak signal value of each said signal sensed;
   and means connected to said passing means for storing each said peak signal value sensed.

4. A fault protection circuit in a medical stimulation unit said unit having an output signal generator therein with a trigger input and a disable input, comprising:
   means for sensing signals emanating from said output signal generator and providing electrical signals representative of the signal current value of said sensed signals, said sensing means being connected to said output signal generator;
   means for establishing an enabling time period, said enabling time period establishing means having its input connected to said output signal generator trigger input;
   means for controllably passing on only the peak value of each of said electrical signals provided by said sensing means, said passing on means being controlled by the output of said time period establishing means;
   means for storing each said peak passed on, said storing means being connected to said passing on means;
   means associated with said storing means for differentiating between successive said values stored by said storing means and for detecting when a threshold differential between successive said values occurs; and
   means connected to said differentiating and detecting means for disabling said signal generator upon the detection of said threshold differential.

5. The circuit of claim 4 wherein said sensing and providing means includes means connected to said output signal generator for passively sensing the current values, as represented by voltage, of said emanating signals, said passive sensing means being connected to said output signal generator; and a first amplifying means connected to said passive sensing means for amplifying said sensed current values represented by voltage; and wherein said peak value storing means includes means for establishing a potential proportional to each said peak value passed on, said potential establishing means being connected to said passing on means; and second amplifying means, sensitive to each said potential established for amplifying each said potential.

6. The circuit of claim 5 wherein said passive sensing means includes a resistor connected in series with an output terminal of said output signal generator, and wherein said first amplifying means includes a first amplifier whose input is tied to said resistor.

7. The circuit of claim 6 wherein said passing on means includes a triggered bilateral switch having its input connected to the output of said first amplifier; and wherein said time period establishing means includes a time delay component connected to said output signal generator trigger and a one-shot monostable multivibrator connected to the output of said time delay, the output of said one-shot being connected to trigger said bilateral switch.

8. The circuit of claim 7 wherein said potential establishing means includes a capacitor connected to said bilateral switch output and wherein said second amplifying means includes a second amplifier having its input tied to said capacitor.

9. The circuit of claim 8 wherein said differentiating and detecting means includes:
   a differentiator connected to the output of said
   a threshold detector connected to the output of said differentiator.

10. The circuit of claim 9 wherein said differentiator includes a high pass filter.

11. The circuit of claim 9 wherein said disabling means includes a latching flip-flop, said flip-flop being input from the output of said threshold detector and having an output connected to the disable input of said output signal generator.

12. The circuit of claim 11 also including a visual display, said display being connected to an output of said latching flip-flop.

13. The circuit of claim 12 wherein said visual display includes a lamp.

14. A fault protection circuit for an electronic pain control device, said device providing outlet signals and having a disable input thereto, comprising:
   means for monitoring said output signals from said device;
   means associated with said monitoring means for detecting an undesirable surge in said output signals provided said detecting means including a rate of change differentiator; and means connected to said detecting means for controlling the operation of said device as a function of said undesirable surge detected.

15. The circuit of claim 14 wherein said device control means includes means, connected to said device disable input, for disabling the output of signals from said device as a function of said undesirable surge detected, said disabling means also being connected to said detecting means;

and wherein said monitoring means includes means for sampling and holding said output signals provided by said device, said sample and hold means being connected to said detecting means and to said device and including means for draining output signals held during said disabling of said device by said control means.

* * * * *

UNITED STATES PATENT AND TRADEMARK OFFICE
CERTIFICATE OF CORRECTION

PATENT NO. : 4,068,669
DATED : January 17, 1978
INVENTOR(S) : Bill Howard Niemi

It is certified that error appears in the above-identified patent and that said Letters Patent are hereby corrected as shown below:

In Column 6, line 47, Claim 9, after "of said" insert --- second amplifier; and ---.

Signed and Sealed this

Twenty-seventh Day of June 1978

[SEAL]

Attest:

RUTH C. MASON
Attesting Officer

DONALD W. BANNER
Commissioner of Patents and Trademarks